United States Patent [19]

Mattila et al.

[11] Patent Number: 6,049,002
[45] Date of Patent: Apr. 11, 2000

[54] METHOD FOR THE PREPARATION OF AQUEOUS SOLUTIONS CONTAINING PERFORMIC ACID AS WELL AS THEIR USE

[75] Inventors: Tapio Mattila, deceased, late of The Hague, Netherlands, by Maire Iida Annikki Mattila, legal representative; Reijo Aksela, Espoo, Finland

[73] Assignee: Kemira Chemicals B.V., Rozenburg, Netherlands

[21] Appl. No.: 08/704,573

[22] PCT Filed: Mar. 9, 1994

[86] PCT No.: PCT/NL94/00059

§ 371 Date: Oct. 28, 1996

§ 102(e) Date: Oct. 28, 1996

[87] PCT Pub. No.: WO95/24388

PCT Pub. Date: Sep. 14, 1995

[51] Int. Cl.[7] .................................................. C23F 11/04
[52] U.S. Cl. .................. 562/6; 562/3; 424/613; 424/616; 422/12; 422/28
[58] Field of Search ............................ 562/6, 3; 422/12, 422/28; 424/613, 616; 514/714

[56] References Cited

U.S. PATENT DOCUMENTS 4,584,390  4/1986  Dieckelmann ........................ 549/526

FOREIGN PATENT DOCUMENTS

| 2008896 | 1/1970 | France . |
| 2101175 | 3/1972 | France . |
| 1962671 | 6/1971 | Germany . |
| 1172514 | 8/1985 | Russian Federation . |

*Primary Examiner*—Samuel Barts
*Attorney, Agent, or Firm*—Young & Thompson

[57] ABSTRACT

The method for the preparation of aqueous solutions containing performic acid formed by reaction of formic acid and hydrogen peroxide n the presence of a catalyst, the catalyst being a compound containing at least one ester group and/or group (a) differing from a carboxylic acid group and an alcoholic group, preferably a carboxylic acid ester, and aqueous solutions containing performic acid, formic acid, hydrogen peroxide, and a compound containing at least one ester group and/or group (a) differing from a carboxylic acid group, and the use of such solutions.

7 Claims, No Drawings

METHOD FOR THE PREPARATION OF AQUEOUS SOLUTIONS CONTAINING PERFORMIC ACID AS WELL AS THEIR USE

BACKGROUND OF THE INVENTION

The present invention relates to a method for the preparation of aqueous solutions containing performic acid formed by reaction of formic acid and hydrogen peroxide in the presence of a catalyst.

DESCRIPTION OF THE RELATED ART

Such a method is known from the book Organic Peroxides, Vol. 1, ed. by B. Swern in 1970 (Wiley Interscience). Dilute performic acid solutions suitable for disinfection are most conveniently prepared by mixing 70–90 wt. % of formic acid and 35–50 wt. % of hydrogen peroxide. Performic acid is unstable at higher concentrations and therefore it is usually prepared by mixing solutions of formic acid and hydrogen peroxide just prior to use (in situ preparation). According to Swern an acid catalyst may be used.

The bactericidal and sporicidal disinfectant properties of performic, peracetic and perproponic acid has been described by Merka et al., in J. Hyg. Epidem. Microbiol. Immunol. 1965 (IX) 220. Performic acid has demonstrated superior results in the studies concerning the fungicidal (mycocidal) properties of these acids (J. Hyg. Epidem. Microbiol. Immunol. 1168, 12, 115).

The exceptional microbicidal properties of performic acid have later been described in EP-A-0 231 623.

A specific use of aqueous performic acid containing solutions is described in not prepublished Dutch patent application 9300445. This reference relates to a method for preventing and combating harmful microorganisms such as fungi, viruses, bacteria, yeasts and algae in water circulation systems, wherein the water including feed solutions and drain water, has a disinfectant added to it which at least comprises performic acid. The contents of this Dutch patent application is incorporated here by reference.

SUMMARY OF THE INVENTION

It is an object of the present invention to increase the equilibrium concentration of performic acid in aqueous solution of formic acid and hydrogen peroxide.

This object was achieved by the use of a compound containing at least one ester group and/or

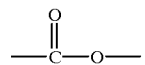

group differing from a carboxylic acid group as a catalyst.

Consequently, the present invention relates to a method for the preparation of aqueous solutions containing performic acid formed by reaction of formic acid and hydrogen peroxide in the presence of a catalyst, characterized in that the catalyst is a compound containing at least one ester group and/or

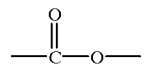

group differing from a carboxylic acid group.

The compound may be used in catalytic amounts, which expression is well-known to one skilled in the art. However, it is preferred that a minimum amount of 10 ppm, calculated on the aqueous solution, is used. In general an amount of more than 10.000 ppm will not bring additional advantages. The particularly preferred range is 200–5000 ppm, again calculated on the total aqueous solution containing the reactants.

Preferably, the catalytic compound is a carboxylic acid ester which is not toxic. However, other ester compounds such as sulfate esters, sulfonate esters/lactones and phosphate esters and similar compounds may be successfully used.

According to a preferred embodiment of the method of the invention the catalytic compound is selected from the group consisting of carboxylic acid esters where the carboxylic acid is:

a) aromatic or aliphatic $C_1$–$C_{20}$ carboxylic acid;

b) aromatic or aliphatic di- or polyfunctional carboxylic acid;

and wherein the alcohol part is a) aliphatic or aromatic $C_1$–$C_6$ mono- of polyfunctional alcohol, b) sugar alcohol, c) polymer containing hydroxyl groups.

Suitable are a.o. compounds like glyceryl mono-, di- and tri-esters, wherein the carboxylic acid is $C_1$–$C_{20}$ carboxylic acid, polymers such as (partially hydrolysed) polyvinylacetate.

The use of the catalyst in accordance with the invention causes an enormous increase, e.g. of 100–300% of the concentration of performic acid. Consequently, performic acid containing preparations prepared in accordance with the invention are more efficient than the prior art solutions.

The present invention also relates to an aqueous solution containing performic acid, formic acid, hydrogen peroxide as well as a compound containing at least one ester group and/or

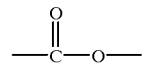

group differing from a carboxylic acid group. The same preferences as mentioned with respect to the method of the invention can be mentioned here.

Further, the invention relates to the use of the above aqueous solutions of the invention for sterilization, sanitization and disinfection purposes. In this respect reference is e.g. made to the above cited EP-A-0 231 623 and NL 9300445.

It appeared from many tests that any compound of the ester type may be used with a certain degree of success. An average chemist will immediately understand what is meant by "ester type".

The inventors find the effect of the ester type compound on the amount of performic acid in the solution surprising.

DESCRIPTION OF THE PREFERRED EMBODIMENTS

The invention is explained in more detail in the following examples.

EXAMPLE 1

A 35% (w/w) solution of hydrogen peroxide (515 g, 5.38 mol) is added dropwise with stirring in 98% (w/w) formic acid (100 ml, 122 g, 2.65 mol) at room temperature. The resulting solution was stirred for 30 minutes at room temperature and diluted with deionized water (1911 g). The solution was divided into 50 ml portions and 50 mg of the following alkyl esters of carboxylic acids were added into each solution:

| Sample | Carboxylic acid ester |
|---|---|
| 1. | no additives |
| 2. | caproic acid mono- and diglyceride (Grinstedt TS-T 104) |
| 3. | 1,2,3-triacetoxypropane |
| 4. | ethyl acetate |
| 5. | methyl formate |
| 6. | sorbitan monolaurate (ICI Span 20) |
| 7. | dibutyl phthalate |

The solutions were allowed to stand at room temperature and the concentrations of hydrogen peroxide and performic acid were determined by titration with Ceric sulfate and sodium thiosulfate, respectively, according to the method of Swern et al. (Swern Organic Peroxides, Vol. 1, page 501, Wiley Interscience, 1970). The concentrations obtained by titrations are collected in tables 1 and 2.

TABLE 1

Concentrations of performic acid obtained from the samples 1–6, 1 hour after dilution.

| Sample No. | additive 1) | performic acid (g/l) |
|---|---|---|
| 1. | no additives | 3.41 |
| 2. | monoglyceride | 6.51 |
| 3. | 1,2,3-triacetoxypropane | 6.51 |
| 4. | ethyl acetate | 6.51 |
| 5. | methylformate | 6.20 |
| 6. | sugar ester | 6.82 |
| 7. | dibutyl phthalate 1,2 | 11.16 |

1) concentration 2500 mg/l
2) titrated after 4 hours stirring at room temperature.

TABLE 2

Concentrations of performic acid obtained from the samples 24 hours after dilution

| Sample No. | additive | performic acid (g/l) |
|---|---|---|
| 1. | no additives | 2.63 |
| 2. | monoglyceride | 6.36 |
| 3. | 1,2,3-triacetoxypropane | 7.13 |
| 4. | ethyl acetate | 7.29 |
| 5. | methylformate | 6.66 |
| 6. | sugar ester | 5.43 |

EXAMPLE 2

A 30 wt. % solution of hydrogen peroxide (610 g, 5.38 mol) was added dropwise into 98 wt. % formic acid (100 ml, 122 g, 2.65 mol). The solution was stirred at room temperature for 30 minutes, whereafter it was divided into five portions. Carboxylic acid esters listed in Table 3, were added into the solutions and they were stirred at room temperature for 4 hours. Concentrations of performic acid and hydrogen peroxide were determined by using the method mentioned above.

TABLE 3

Concentrations of performic acid obtained from the samples 4 hours after dilution.

| Sample | additive | (mg/l) | performic acid (mg/l) |
|---|---|---|---|
| 1. | no additives | | 27.28 |
| 2. | ethyl acetate | 1300 | 31.00 |
| 3. | ethyl propionate | 1500 | 28.52 |
| 4. | dibutyl phthalate | 2500 | 31.93 |
| 6. | glycolic acid butyl ester | 1500 | 44.64 |

It is claimed:

1. A method for the preparation of aqueous solutions comprising performic acid formed by reaction of formic acid and hydrogen peroxide in the presence of a catalyst, wherein the catalyst is a compound containing at least one ester group.

2. The method according to claim 1, wherein the catalyst is present in an amount of 100–5000 ppm, calculated on the aqueous solution.

3. The method according to claim 1, wherein the catalytic compound is a carboxylic acid ester.

4. The method according to claim 1, wherein the catalytic compound is selected from the group consisting of carboxylic acid esters where the carboxylic acid is:

a) aromatic or aliphatic $C_1$–$C_{20}$ carboxylic acid;
　b) aromatic or aliphatic polyfunctional carboxylic acid;
　and wherein the alcohol part is:
　　a) aliphatic or aromatic mono- or polyfunctional $C_1$–$C_6$ alcohol;
　　b) sugar alcohol,
　　c) polymer containing alcohol groups.

5. A method for sterilization, sanitization and disinfection purposes, comprising applying to a solid surface an aqueous solution comprising performic acid, formic acid, hydrogen peroxide and a compound containing at least one ester group in catalytic amounts as a stabilizer.

6. The method of claim 1, wherein the catalytic compound comprising

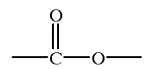

group differing from a carboxylic acid group.

7. The method of claim 1, wherein the catalytic compound is selected from the group consisting of sulfate esters, sulfonate esters, lactones and phosphate esters.

* * * * *